United States Patent [19]

Engel et al.

[11] 4,189,494
[45] Dec. 19, 1980

[54] REDUCING FREE FATTY ACID OF THE BLOOD AND SUPPRESSING APPETITE

[75] Inventors: Günter Engel, Weil, Fed. Rep. of Germany; Heribert Wagner, Pfeffingen, Switzerland

[73] Assignee: Sandoz Ltd., Basel, Switzerland

[21] Appl. No.: 879,345

[22] Filed: Feb. 21, 1978

Related U.S. Application Data

[63] Continuation of Ser. No. 737,442, Nov. 1, 1976, abandoned.

[30] Foreign Application Priority Data

Nov. 6, 1975 [GB] United Kingdom ............... 46034/75

[51] Int. Cl.$^2$ ............................................. A61K 31/40
[52] U.S. Cl. ................................................... 424/274
[58] Field of Search ......................................... 424/274

[56] References Cited

U.S. PATENT DOCUMENTS 3,705,907 12/1972 Troxler ....................... 260/326.14 R

*Primary Examiner*—Stanley J. Friedman

*Attorney, Agent, or Firm*—Gerald D. Sharkin; Robert S. Honor

[57] ABSTRACT

The present invention provides a new use of the compounds of formula I,

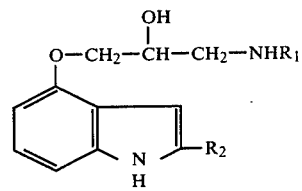

wherein
  $R_1$ is lower alkyl, cycloalkyl having 3 to 4 carbon atoms, phenylalkyl of 8 to 10 carbon atoms or 1-adamantyl, and
  $R_2$ is hydroxymethyl, carboxyl or lower alkoxycarbonyl, as agents for the treatment or prevention of myocardism or as appetite suppressants.

11 Claims, No Drawings

REDUCING FREE FATTY ACID OF THE BLOOD AND SUPPRESSING APPETITE

This is a continuation of application Ser. No. 737,442 filed Nov. 1, 1976, now abandoned.

The present invention relates to a new use of the compounds of formula

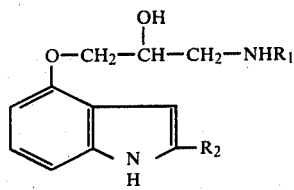

wherein
- $R_1$ is lower alkyl, cycloalkyl having 3 to 4 carbon atoms, phenylalkyl of 8 to 10 carbon atoms or 1-adamantyl, and
- $R_2$ is hydroxymethyl, carboxyl or lower alkoxycarbonyl.

The compounds of formula I are known. They are, for example, disclosed in U.S. Pat. No. 3,705,907 as β-adrenergic agents. It has now been found that the compounds are particularly useful as inhibitors of mobilisation of animal energy reserves, induced by emotional stress, e.g. by catecholamine secretion.

For example, the compounds inhibit the increased free fatty acid concentration in the blood, and the lipolysis effect, induced by emotional stress, as indicated by an inhibition of glycerol release stimulated by isoproterenol in standard tests, e.g. as follows:

(i) In vitro

Isolated fat cells are obtained from dog sub-cutaneous tissue, and from rat and guinea pig epididymal fat pads, in accordance with the method of M. Rodbell [J. Biol. Chem. 239, 375–380 (1964)]. Cells from one of the animals are dispersed in Krebs phosphate buffer containing 4% bovine serum albumin. 1 ml aliquots of the cell suspension in plastic incubation flasks are treated with the test substance at $10^{-9}$ to $10^{-7}$ Molar and isoproterenol at $10^{-7}$ Molar. The glycerol release is determined in conventional manner, e.g. according to the method of S. Laurell et al, Helv. Chim. Acta. 13, 317–322 (1966).

(ii) In vivo

Rats are fasted for 16 hours. A sub-cutaneous injection of 400 μg/kg of isoproterenol results in a glycerol concentration in the blood plasma of 400% the original value. This increased glycerol concentration remains constant for ca. 60 minutes and acts as a control value. The test substance is administered at a dose of from about 0.001 to about 0.01 mg/kg for i.v. administration, and of from about 0.01 to about 0.1 mg/kg for p.o. administration, 10 minutes before the isoproterenol injection, and the animals are decapitated 40 minutes after the isoproterenol injection. The glycerol concentration in the blood is calculated in conventional manner, e.g. using the conventional glycero-3-phosphate-dehydrogenase method [according S. Laurell et al; reference as mentioned above].

By virtue of their effect in reducing the increases in free fatty acid concentration in blood plasma, the compounds are therefore useful in the treatment of acute myocardial infarction in animals, resulting inter alia in a decrease in the risk of ventricular arrhythmias and further myocardial ischemic injury.

As indicated by the above, the compounds are additionally useful in the prophylaxis of myocardism in animals suffering from a myocardial ischemic injury, e.g. due to arteriosclerosis in the heart coronary arteries. Administration of the compounds prevents inter alia an increase in the ischemic zone in the heart and the anaerobic metabolic condition of the heart.

The compounds of formula I additionally inhibit hyperglycemia induced by emotional stress, as indicated by an inhibition of glycogenolysis in standard tests, as follows:

In the above-mentioned rat in vivo test the glucose concentration in the blood is determined in conventional manner, e.g. using the ferricyanide method. In the control animals the glucose concentration doubles after 40 minutes after isoproterenol administration. The compounds are administered parenterally at a dose of from about 0.01 to about 10 mg/kg animal body weight.

By virtue of their effect in the above test the compounds are therefore further useful as suppressants of appetite, e.g. induced by emotional stress. Such stress conditions are well appreciated in the art, e.g. see M. Carruthers et al, in D. M. Burley et al: New Perspectives in beta-blockade, Int. Symposium Scanticon, Aarhus, Denmark, p. 275, 1972, and may include emotional stresses associated with car driving, speaking in public, and preparing for parachuting.

For the above-mentioned uses the dosage will, of course, vary depending on the compound employed, mode of administration and treatment desired. However, in general, satisfactory results are obtained with a daily dosage of from about 0.01 to about 10 mg/kg animal body weight, conveniently given in divided doses 2 to 4 times a day or in sustained release form. For the larger mammal, the total daily dosage is in the range from about 1 to about 300 mg, preferably, however, 5 to 30 mg, and dosage forms suitable for oral or parenteral administration comprise from about 0.25 to about 150 mg of the compounds admixed with a solid or liquid pharmaceutical carrier or diluent.

The compounds may be administered in free base or in pharmaceutically acceptable acid addition salt form. Such salt forms exhibit the same order of activity as the free base forms, and may be prepared in conventional manner. Such salt forms are known and include the hydrogen malonate.

Pharmaceutical compositions comprising a compound of formula I in free base or in pharmaceutically acceptable acid addition salt form in association with a pharmaceutical carrier or diluent may be used for the administration of the compounds. Such compounds are in general known and may be formulated in conventional manner to be, for example, a tablet or solution.

From the standpoint of ease of administration, solid forms are preferred.

In the above formula "lower alkyl or alkoxy" preferably has from 1 to 4 carbon atoms. $R_1$ is preferably lower alkyl, especially branched in the α-position. $R_2$ is preferably lower alkoxycarbonyl, the alkyl moiety thereof preferably being branched in the α-position.

The preferred compound is 4-(3-tert.-butylamino-2-hydroxypropoxy)indole-2-carboxylic acid isopropyl ester.

The following Examples illustrate compositions for use in the process of the invention.

EXAMPLE 1: Hard gelatine capsules

Hard gelatine capsules having the following compositions may be formulated in conventional manner and administered for the use mentioned above 2 to 4 times a day.

| | | |
|---|---|---|
| 4-(tert.-butylamino-2-hydroxypropoxy)-indole carboxylic acid isopropyl ester hydrogen malonate | 5 | mg |
| Lactose | 735 | mg |
| Corn starch | 25 | mg |
| Magnesium stearate | 1.0 | mg |
| Colloidal silica | 0.5 | mg |

EXAMPLE 2: Tablets

Tablets having the following composition may be made in conventional manner, and used for the above-mentioned uses 2 to 4 times a day.

| | | |
|---|---|---|
| 4-(tert.-butylamino-2-hydroxypropoxy)-indole carboxylic acid isopropyl ester hydrogen malonate | 5 | mg |
| Lactose | 83.8 | mg |
| Corn starch | 13.0 | mg |
| Magnesium stearate | 1.0 | mg |
| Colloidal silica | 0.2 | mg |

We claim:

1. A method of reducing free fatty acid concentration in the blood of an animal in need of such treatment, comprising administering to said animal a therapeutically effective amount of a compound of the formula I

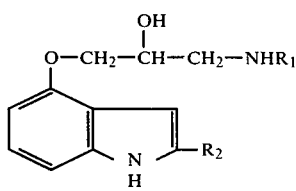

wherein
$R_1$ is lower alkyl, cycloalkyl having 3 to 4 carbon atoms, phenylalkyl of 8 to 10 carbon atoms or 1-adamantyl, and
$R_2$ is hydroxymethyl, carboxyl or lower alkoxycarbonyl,
or a pharmaceutically acceptable acid addition salt thereof.

2. A method of claim 1, wherein the compound is 4-(3-tert.-butylamino-2-hydroxypropoxy)indole-2-carboxylic acid isopropyl ester.

3. A method of claim 1, wherein the compound is 4-(3-tert.-butylamino-2-hydroxypropoxy)indole-2-carboxylic acid isopropyl ester.

4. A method of claim 2, wherein the daily dose is from 0.01 to 10 mg/kg.

5. A method of claim 3, wherein the daily dose is from 0.01 to 10 mg/kg.

6. A method of claim 4, wherein the daily dose is from 1 to 300 mg.

7. A method of claim 5, wherein the daily dose is from 1 to 300 mg.

8. A method of claim 6, wherein the daily dosage is administered 2 to 4 times a day in unit dosage form.

9. A method of claim 7, wherein the daily dosage is administered 2 to 4 times a day in unit dosage form.

10. A method of suppressing the appetite in animals, comprising administering an appetite suppressing effective amount of a compound of formula I:

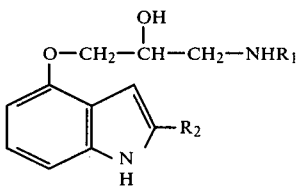

wherein
$R_1$ is lower alkyl, cycloalkyl having 3 to 4 carbon atoms, phenylalkyl of 8 to 10 carbon atoms or 1-adamantyl, and
$R_2$ is hydroxymethyl, carboxyl or lower alkoxycarbonyl,
or a pharmaceutically acceptable acid addition salt thereof to an animal in need of such treatment.

11. A method of suppressing in animals appetite caused by hyperglycemia resulting from emotional stress, comprising administering an appetite suppressant effective amount of a compound of formula I:

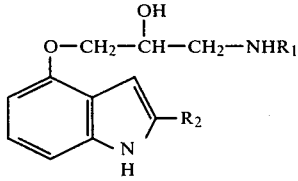

wherein
$R_1$ is lower alkyl, cycloalkyl having 3 to 4 carbon atoms, phenylalkyl of 8 to 10 carbon atoms or 1-adamantyl, and
$R_2$ is hydroxymethyl, carboxyl or lower alkoxycarbonyl,
or a pharmaceutically acceptable acid addition salt thereof to an animal in need of such treatment.

* * * * *